(12) United States Patent
Hoeg et al.

(10) Patent No.: US 8,817,086 B2
(45) Date of Patent: *Aug. 26, 2014

(54) IMAGE ORIENTING COUPLING ASSEMBLY

(75) Inventors: Hans David Hoeg, Arcadia, CA (US);
Eric L. Hale, Altadena, CA (US);
Nathan Jon Schara, Pasadena, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 167 days.

This patent is subject to a terminal disclaimer.

(21) Appl. No.: 13/076,561

(22) Filed: Mar. 31, 2011

(65) Prior Publication Data

US 2011/0175991 A1 Jul. 21, 2011

Related U.S. Application Data

(63) Continuation of application No. 11/355,345, filed on Feb. 16, 2006, now Pat. No. 7,956,887.

(60) Provisional application No. 60/653,927, filed on Feb. 17, 2005.

(51) Int. Cl.
*H04N 9/47* (2006.01)
*H04N 5/228* (2006.01)

(52) U.S. Cl.
USPC .......................................... 348/65; 348/208.99

(58) Field of Classification Search
USPC .......... 600/117, 101, 109; 348/65, 68, 73, 76, 348/208.99, 208.1, 208.2, 208.4, 208.5, 348/208.6, 208.7, 208.8, 208.11, 335, 340
See application file for complete search history.

(56) References Cited

U.S. PATENT DOCUMENTS

| | | | | |
|---|---|---|---|---|
| 4,503,842 A | * | 3/1985 | Takayama | 600/152 |
| 4,991,957 A | * | 2/1991 | Sakamoto et al. | 356/241.4 |
| 5,307,804 A | | 5/1994 | Bonnet | |
| 5,359,992 A | * | 11/1994 | Hori et al. | 126/4 |
| 5,645,065 A | * | 7/1997 | Shapiro et al. | 600/424 |
| 5,677,763 A | | 10/1997 | Redmond | |
| 5,899,851 A | | 5/1999 | Koninckx | |
| 6,030,339 A | | 2/2000 | Tatsuno et al. | |

(Continued)

FOREIGN PATENT DOCUMENTS

| | | |
|---|---|---|
| JP | 6237881 A | 8/1994 |
| JP | 10262921 A | 10/1998 |

OTHER PUBLICATIONS

European Search Report; Application No. EP 60 00 3323; May 21, 2010; 8 pages.

*Primary Examiner* — Nicholas Giles
(74) *Attorney, Agent, or Firm* — St. Onge Steward Johnston & Reens LLC (57) ABSTRACT

A coupling assembly for a scope and an image sensor housing is disclosed generally comprising an image orientation unit having first and second coupling sections for coupling the unit to a scope and an image sensor housing, such as a camera head, an optical assembly with a rotatable optical element for rotating the images, a rotation sensor for monitoring rotation of the optical element, an accelerometer for monitoring rotation of the unit, and a processor for receiving signals from the rotation sensor and the accelerometer and calculating the orientation of the images relative to the direction of gravity. In certain embodiments, the processor causes an actuator to rotate the optical element to level the images. In some embodiments, the processor activates a visual indicator, such as a diode, to indicate the direction of vertical.

25 Claims, 6 Drawing Sheets

(56) References Cited

U.S. PATENT DOCUMENTS

| | | | |
|---|---|---|---|
| 6,097,423 A | 8/2000 | Mattsson-Boze et al. | |
| 6,471,637 B1 | 10/2002 | Green et al. | |
| 2002/0161280 A1* | 10/2002 | Chatenever et al. | 600/112 |
| 2004/0210105 A1 | 10/2004 | Hale et al. | |
| 2005/0154260 A1 | 7/2005 | Schara et al. | |
| 2005/0228230 A1 | 10/2005 | Schara et al. | |

* cited by examiner

IMAGE ORIENTING COUPLING ASSEMBLY

CROSS-REFERENCE TO RELATED APPLICATIONS

The present application is a continuation of U.S. patent application Ser. No. 11/355,345, filed on Feb. 16, 2006, now U.S. Pat. No. 7,956,887 which application claims the benefit of, under Title 35, United States Code, Section 119(e), U.S. Provisional Patent Application No. 60/653,927, filed Feb. 17, 2005. All prior applications are herein incorporated by reference.

FIELD OF THE INVENTION

The present invention relates to an assembly for orienting images obtained by a viewing instrument, such as an endoscope. More specifically, the invention relates to a coupling assembly to connect an endoscope to a sensor housing, such as a camera, that orients the images for the user by automatically leveling them or providing an indication of the vertical direction.

BACKGROUND OF THE INVENTION

Various types of viewing scopes, such as endoscopes, are generally well known in the art. Generally, an endoscope is a medical device for insertion into a body passageway or cavity that enables an operator to view and/or perform certain surgical procedures at a site inside a patient's body. As is known, endoscopes may be either rigid or flexible, and generally include a long tubular member equipped with, for example, some type of system for transmitting images to the user, and in some cases, a working channel for a surgical instrument.

More specifically, the scope itself generally comprises an elongated shaft having a distal end and a proximal end, and at least one internal passageway extending between the distal end and the proximal end. Optics are disposed at the distal end of the shaft and extend through an internal passageway of the shaft, such that the optics can capture an image of a selected region located near the distal end of the shaft and convey that image to the proximal end of the shaft. An image sensor, such as a camera, is disposed adjacent to the proximal end of the shaft, such that the image obtained and transmitted by the optics can be conveyed to a display device to be viewed by a physician.

One problem with such systems, however, is that, as a surgeon manipulates the scope and camera, the camera faithfully relates what it sees, with its own upright axis displayed as the upright axis of the image on the display, which often results in rotation of the images being viewed. As the image rotates, the surgeon loses track of which direction is actually up inside the endoscopic cavity. This disorientation is one of the major challenges in endoscopy, and, at times, has resulted in severe mistake such as the snipping of optical nerves that, during the procedure, were believed to be a different part of the anatomy. Accordingly, the surgeon must continuously try to correlate his own mental picture of the anatomy with the endoscopic picture of the display. Indeed, the need to be sure of which direction is up is so important that it has become common for surgeons to observe the flow direction of fluid droplets on the endoscope cover window or search for pooling blood in order to get a sense of direction inside the cavity. Additionally, besides the importance of being able to distinguish between anatomical features that look similar, it is also important to be sure of the up direction in order to help understand the position of the scope relative to the surrounding anatomy.

Accordingly, a number of systems have been proposed to maintain the proper upright, gravity-leveled orientation of the endoscopic images irrespective of how the endoscope is being manipulated. Examples, of such systems are described in U.S. Pat. No. 5,307,804 to Bonnet, U.S. Pat. No. 5,899,851 to Koninckx, U.S. Pat. No. 6,097,423 to Mattsson-Boze, et al., U.S. Pat. No. 6,471,637 to Green, et al., U.S. Patent Application No. 2002/0161280 by Chatenever, et al., U.S. Patent Application No. 2004/0210105 by Hale, et al., and U.S. Patent Application No. 2005/0228230 by Schara, et al.

Figures 1A, 1B, 1C:
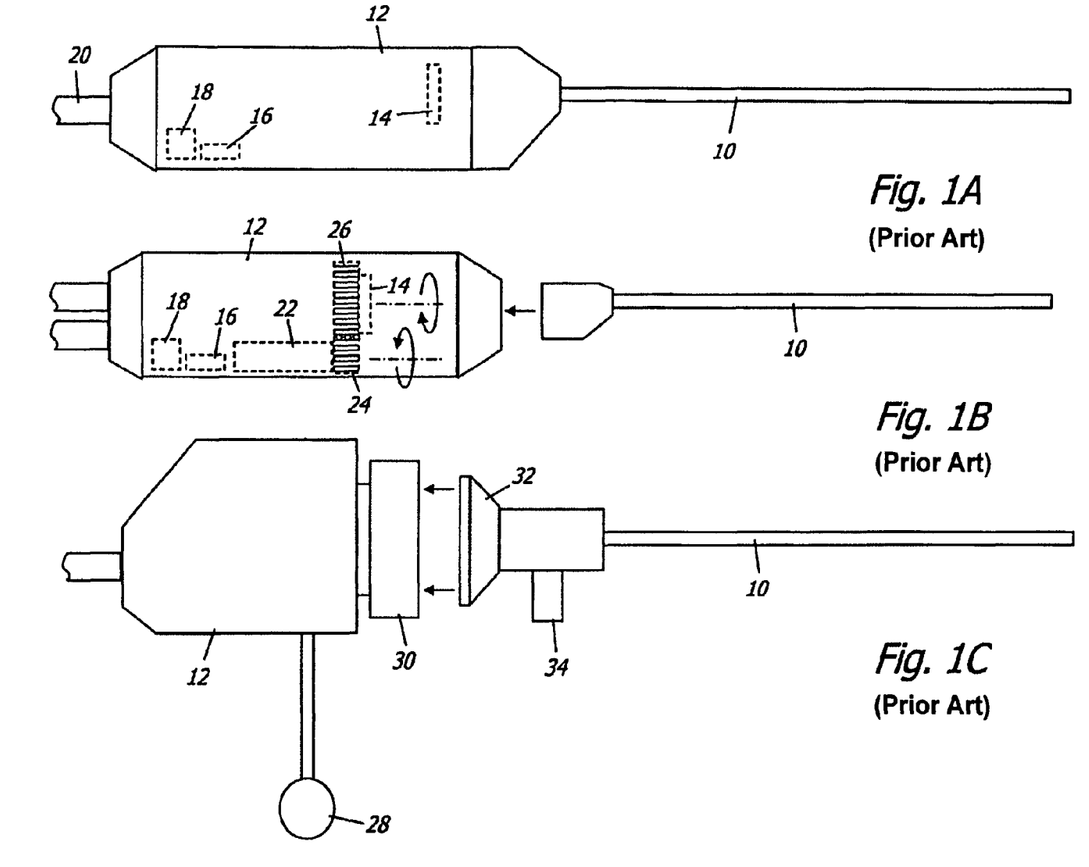
FIGS. 1A-C are side views of image orientation systems in the prior art.

The basic known designs of gravity-leveled endoscopic systems are illustrated in FIGS. 1A-C. FIG. 1A shows an endoscope that has an integrated shaft 10 and camera head 12. In addition to an image sensor 14, the camera head 12 also houses a processor 16 and rotation sensor 18. Power and electronic communication is provided through a cable 20. The image rotation required to level the image is done electronically by a separate processor (not shown). Because this integrated camera endoscope is a single unit, it is not compatible with the traditional endoscopes and camera heads most commonly available in the operating room, and a prospective user must buy the whole system in order to obtain gravity-leveling capabilities.

FIG. 1B shows a gravity-leveled system that has a shaft 10 that is detachable from the camera head 12, which also houses a processor 16 and a rotation sensor 18. Image leveling is accomplished by physically rotating an image sensor 14 with a motor 22 and gear train 24, 26. A disadvantage of this system is that the camera head 12 is not compatible with the standard eyepiece of traditional endoscopes, but rather, requires a special coupling between the camera head and the endoscope shaft.

FIG. 1C illustrates a camera head 12 with an eyepiece coupler 30 and pendulum 28, which seeks the upright camera position by the nature of its weight. While compatible with a traditional endoscope with an eyepiece 32 and a light post 34, one disadvantage of this solution is that the pendulum 28 is cumbersome and becomes unresponsive as it approaches horizontal. Additionally, it requires the purchase of this specialty camera head, even if a traditional camera head is already available. Finally, these systems typically do not provide gravity-leveling for rigid endoscopes with an off-axis view vector.

What is desired, therefore, is a system for orienting the images obtained by a scope independently of the orientation of the scope. What is further desired is a system for orienting the images obtained by a scope that can be employed with standard camera heads and scopes. What is also desired is a system for orienting the images obtained by a scope that is accurate, not cumbersome, and can be used with scopes having an off-axis view vector.

SUMMARY OF THE INVENTION

Accordingly, it is an object of the present invention to provide an assembly for orienting the images obtained by a scope that can accurately monitor the orientation of the scope regardless of how it is manipulated.

It is a further object of the present invention to provide an assembly for orienting the images obtained by a scope that can couple a traditional endoscope to a standard camera head.

It is yet another object of the present invention to provide an assembly for orienting the images obtained by a scope that is compact.

It is still another object of the present invention to provide an assembly for orienting the images obtained by a scope that works with an off-axis view vector.

In order to overcome the deficiencies of the prior art and to achieve at least some of the objects and advantages listed, the invention comprises a coupling assembly for connecting a scope and image sensor housing, including a image orientation unit having first and second ends, the unit having a first coupler section located at the first end of the unit for coupling the unit to a scope and a second coupler section located at the second end of the unit for coupling the unit to an image sensor housing, an optical assembly at least partly arranged in the unit for transmitting images therethrough, the optical assembly having at least one rotatable optical element that rotates the optical images, a rotation sensor for monitoring rotation of the optical element and generating a first signal therefor, an accelerometer arranged in the image orientation unit for monitoring the rotation of the unit and generating a second signal therefor, and a processor connected to the rotation sensor and the accelerometer for receiving the first and second signals and, at least partly based on the first and second signals, calculating the orientation of the images relative to the direction of gravity.

In another embodiment, the invention comprises a coupling assembly connecting a scope and image sensor housing, including an image orientation unit having first and second ends, a scope coupled to the first end of the image orientation unit, an image sensor housing coupled to the second end of the image orientation unit, an optical assembly at least partly arranged in the unit for transmitting images therethrough, the optical assembly having at least one rotatable optical element that rotates the optical images, a rotation sensor for monitoring rotation of the optical element and generating a first signal therefor, an accelerometer arranged in the image orientation unit for monitoring the rotation of the unit and generating a second signal therefor, and a processor connected to the rotation sensor and the accelerometer for receiving the first and second signals and, at least partly based on the first and second signals, calculating the orientation of the images relative to the direction of gravity.

In yet another embodiment, the invention comprises an endoscopic assembly, including a camera, the camera comprising a main section and a coupling assembly section, an optical assembly arranged in the camera for transmitting images therethrough, the optical assembly having at least one optical element, a rotation sensor arranged in the camera for monitoring rotation of the optical element and generating a first signal therefor, an accelerometer arranged in the coupling assembly section for monitoring the rotation of the coupling assembly section and generating a second signal therefor, and a processor connected to the rotation sensor and the accelerometer for receiving the first and second signals and, at least partly based on the first and second signals, calculating the orientation of the images relative to the direction of gravity.

In some of these embodiments, the invention further includes an actuator, such as a motor, for rotating the optical element, wherein the actuator is connected to the processor to receive a signal therefrom indicating the amount to rotate the optical element in order to level the images. In some embodiments, the optical element is disposed in an optical element housing, a first gear is coupled to the motor and rotated thereby, and a second gear is driven by the first gear and coupled to the optical element housing such that the optical element is rotated by rotation of the second gear.

In some embodiments, the orientation unit includes a main housing, the second coupling section of the orientation unit includes a rotatable member that rotates relative to the main housing, and the optical element housing is coupled to the rotating member such that it rotates with the rotating member relative to the main housing, and the motor drives a differential gear set coupled to the optical element housing such that the optical element is rotated thereby.

In certain embodiments, the optical assembly includes a second rotatable optical element, and a second rotation sensor monitors rotation of the second optical element and generates a third signal therefor, wherein the processor is connected to the second rotation sensor for also receiving and using the third signal to calculate the orientation of the images relative to the direction of gravity.

In some embodiments, the actuator is connected to the processor to receive a signal therefrom indicating the amount to rotate the optical assembly in order to level the images, wherein the orientation unit includes a main housing, the second coupling section of the orientation unit includes a rotatable member that rotates relative to the main housing, and the optical assembly is coupled to the rotating member such that the optical assembly rotates with the rotating member relative to the main housing.

In certain embodiments, the invention further includes a rotatable image sensor for receiving the images transmitted by the optical assembly, wherein the image sensor is connected to the processor and is rotated based on the first and second signals.

In some embodiments, the orientation unit includes a visual indicator that indicates the direction of vertical based on the signal provided by the accelerometer. In some of these embodiments, the visual indicator comprises an array of diodes, wherein the diodes are individually illuminated to indicate the direction of vertical.

DETAILED DESCRIPTION OF THE INVENTION

Figure 2A:
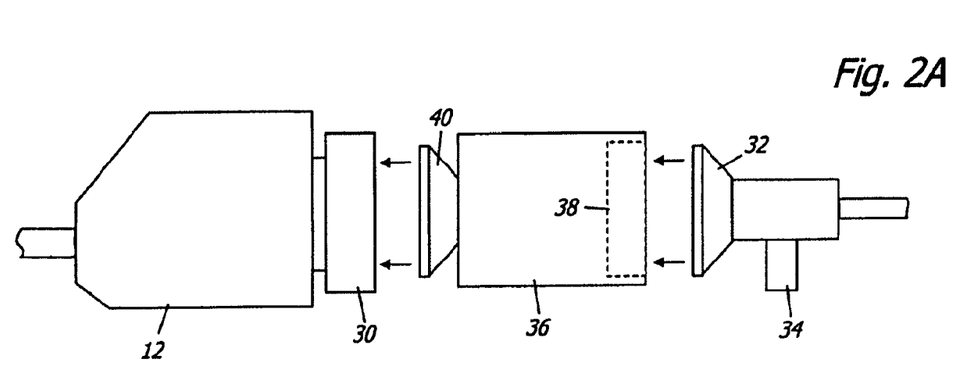
FIG. 2A is a side view of an image orienting coupling assembly in accordance with the invention.
Figure 2B:
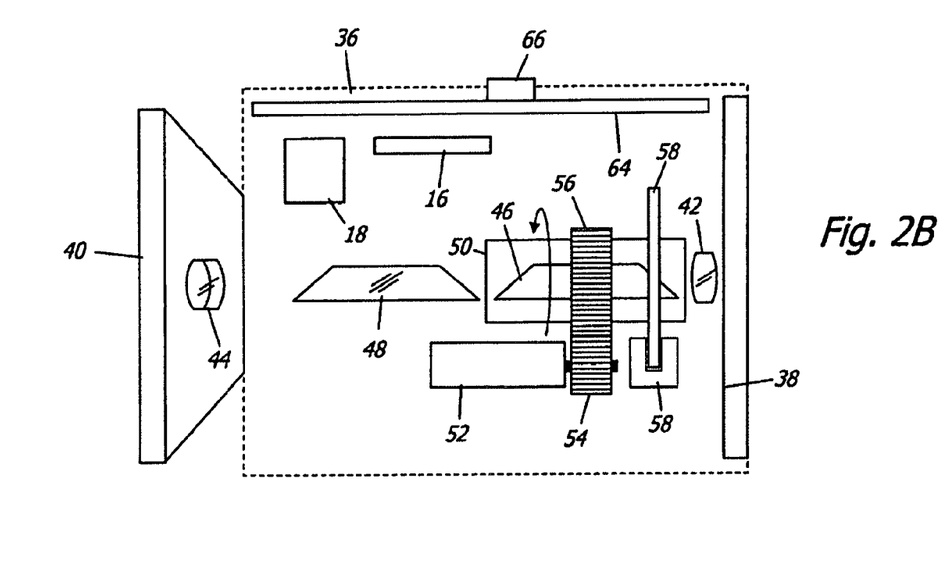
FIG. 2B is an exposed side view of the image orientation unit of the image orienting coupling assembly of FIG. 2A.

The basic components of one embodiment of an image orienting coupling assembly in accordance with the invention are illustrated in FIGS. 2A-B. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

An image orientation unit 36 has a first end with a coupling section 38, which comprises a standard coupler for connecting to a traditional endoscope eyepiece 32, and a second end with a coupling section 40, which may comprise its own eyepiece 40 that is connected to a traditional camera head 12 via an eyepiece coupler 30. The image orientation unit 36 has an optical assembly arranged therein for transmitting the endoscopic images from the scope to the camera, which is further explained below. An accelerometer 18 is arranged the unit 36, which gauges any rotation of the unit 36 relative to the direction of gravity, as well as the inclination of the unit. The accelerometer 18 generates and communicates a signal reflecting this rotation to a processor 16 connected thereto.

In certain advantageous embodiments, the optical assembly includes a series of lenses 42, 44, an optical image rotator 46, and an optical image reverser 48. The image rotator 46 comprises a rotatable optical element, such as, for example, a dove prism or a K prism. The optical element 46 is at least partly disposed in a housing 50, and the housing 50 is coupled to a gear 56. Another gear 54, which is rotated by an actuator 52, engages the gear 56. In this way, the actuator 52, such as a motor, causes the optical element 46 to rotate via the gear set 54, 56. A rotation sensor, such as an encoder 58, monitors the rotation of the prism 46 and, like the accelerometer 18, generates and communicates a rotation signal to the processor 16, which is likewise connected thereto. The processor 16 uses the information received in these first and second signals respecting the rotation of the optical element 46 and the unit 36 to calculate the amount of rotation required to level the endoscopic image, and accordingly provides a signal to the actuator 52 to rotate the element 46 about the optical axis the appropriate amount.

In some embodiments, the orientation unit 36 is powered via a cable, while in other advantageous embodiments, it is powered by an on-board rechargeable battery 64 with a recharging connector 66.

In certain embodiments, the orientation unit 36 is tightly clamped to the endoscope eyepiece 32 so that, by monitoring the rotation of the unit 36, the accelerometer 18 also monitors the rotation of the endoscope. Similarly, the camera head 12 is clamped tightly to the eyepiece 40 such that there is no relative rotation between the camera head 12 and the eyepiece 40. As a result, the camera head 12 always has a known orientation relative to the orientation unit 36 so that the processor 16 can compute the correct adjustments for the rotator prism 46 without additional sensors. The initial alignment of the endoscope, orientation unit 36, and camera head 12 is done at the beginning of each procedure according to external calibration marks or indicators, such as notches or lines.

Figure 3A:
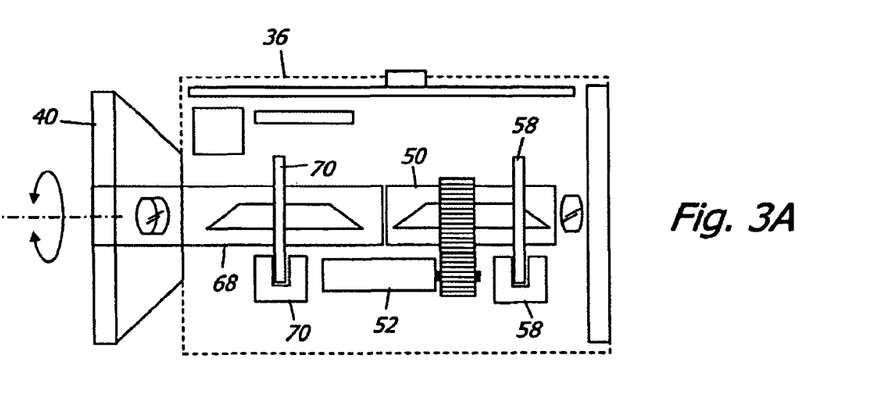
FIGS. 3A-C are side views showing additional detail of the image orientation assembly of FIGS. 2A-B.

In certain embodiments, as illustrated in FIG. 3A, the orientation unit 36 allows the eyepiece 40 and an optical housing tube 68 to rotate independently of the orientation unit 36. This independent rotation gives the camera head the freedom to rotate relative to the endoscope, as is desired in some endoscopic procedures. For example, surgeons sometimes like to hold the camera head and grab the endoscopic light cable to rotate the endoscope, requiring relative rotation between the camera head and the endoscope. Accordingly, in order to achieve this increased flexibility, a second encoder 70 is used to monitor the relative rotation between the camera head and the orientation unit 36 rigidly connected to the endoscope. The encoder 70 is connected to the processor 16 and sends a signal thereto reflecting the rotation of the camera head relative to the unit 36, and the processor uses this information, along with the information received from the accelerometer 18 and encoder 58, to calculate the amount the actuator 52 must rotate the optical element housing 50 in order to level the endoscopic image.

Figure 3B:
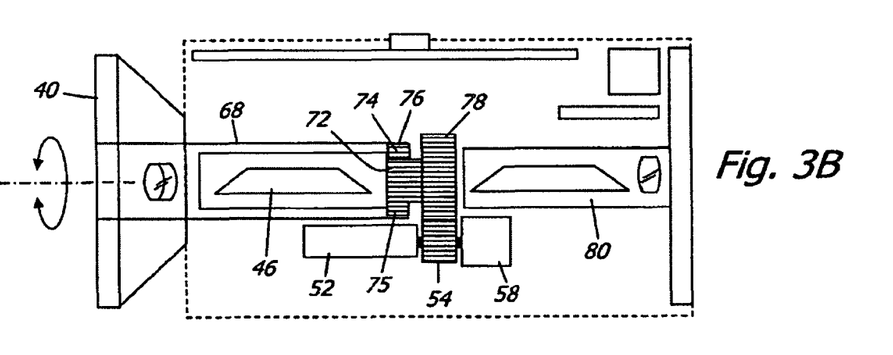

As shown in FIG. 3B, in some embodiments, the prism 46 is positioned in the rear of the unit 36 in the optical housing tube 68, and the forward prism assembly 80 remains fixed to the housing of the orientation unit 36. Accordingly, the prism 46 rotates with the camera head 12, and a differential gear drive can be used instead of a second encoder. Such a differential drive includes an appropriate set of gears 72, 74, 75, 76, 78 with the correct ratio to allow the eyepiece 40 and the actuator 52 to drive rotator prism 46 independently, such that the image stays leveled regardless of the position of the unit/endoscope combination relative to the camera head. The encoder 58 indirectly senses the rotation of the rotator prism 46 by sensing the rotation of the drive gear 54.

Figure 3C:
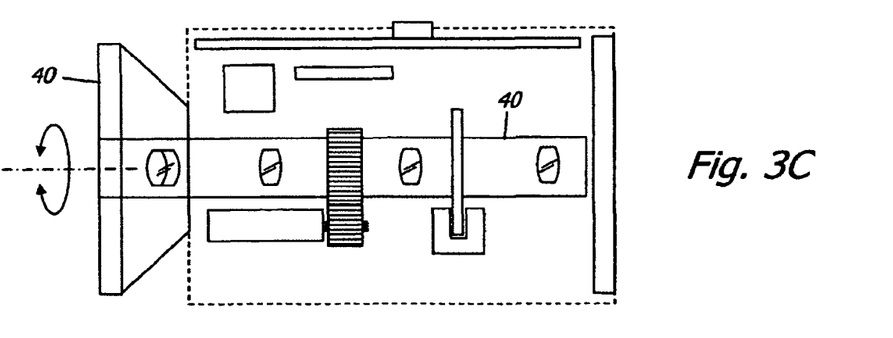

As shown in FIG. 3C, in some embodiments where it is desired to permit the camera head to rotate relative to the endoscope, instead of using a prism to rotate the image, an entire optics-eyepiece assembly 40 is rotated. Because the attached camera head rotates with the entire assembly 40, the image leveling is accomplished by rotating the camera itself instead of the optical image. In this case, the user holds the endoscope or orientation unit instead of the camera, and the motor 52, which receives its instructions from the processor 16 based on the signals received from the accelerometer 18 and encoder 58, rotates the entire assembly 40 via a standard gear set 54, 56, as previously explained.

Figure 4:
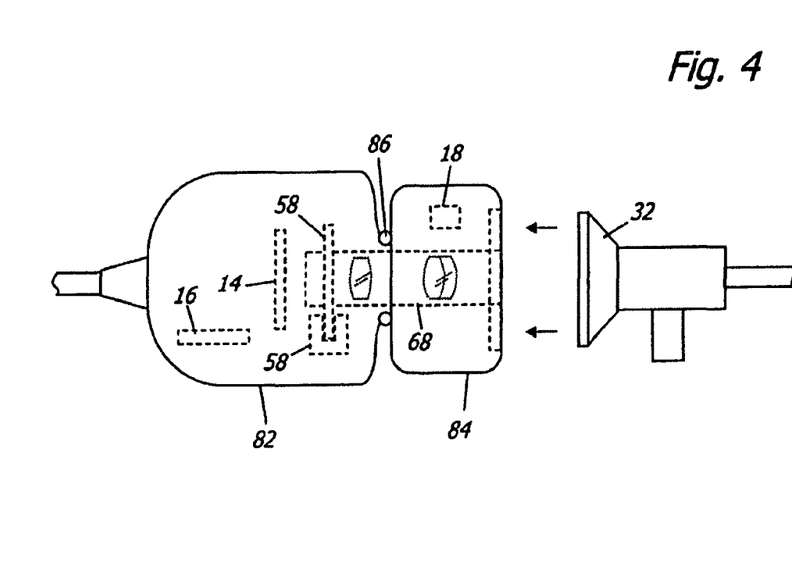
FIG. 4 is a side view of an endoscopic camera employing an image orientation unit in accordance with the invention.

Referring to FIG. 4, a specialty camera head is illustrated that includes the above described image-leveling. The camera head includes a main section 82 and coupling assembly 84. The coupling assembly 84, which can rotate relative to the main section 82 through a coupling joint 86, clamps rigidly to an endoscope eyepiece 32 and houses an accelerometer 18. Because this coupling assembly 84 clamps rigidly to an endoscope eyepiece 32, the accelerometer 18 follows and senses the motion of the endoscope. The main section 82, which comprises an image sensor 14, an encoder 58, and supporting electronics (not shown) can spin freely relative to the endoscope, just like a standard camera head. The encoder 58 senses the rotation of the optics assembly 68, which is partly disposed in the coupling assembly 84. The processor 16 calculates an up-right image orientation in response to signals from the accelerometer 18 and encoder 58, as previously described. The image orientation is then adjusted electronically, or by rotating the image sensor 14, or by rotating a rotator prism, which may be arranged in the camera head.

Figures 5A, 5B, 5C:
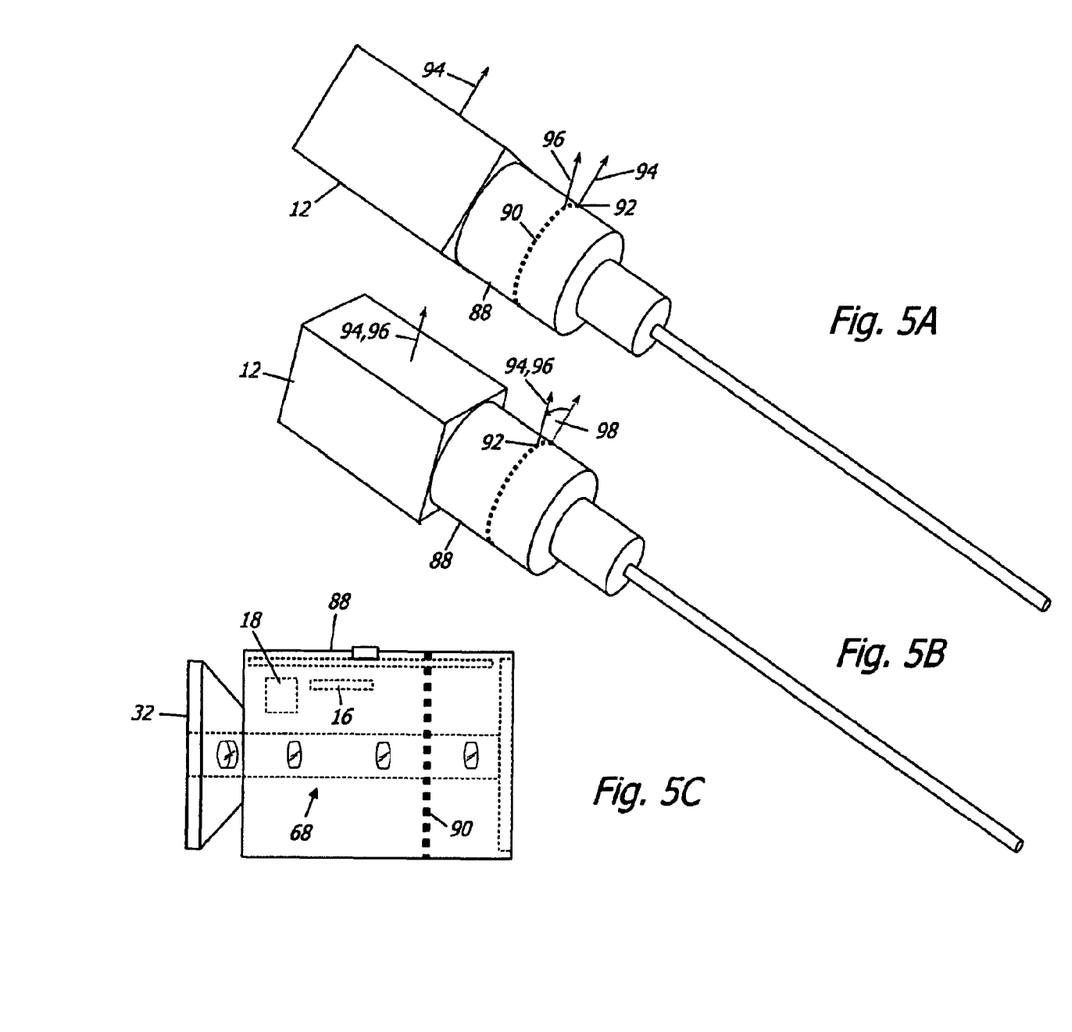
FIGS. 5A-B are isometric views of an endoscopic system in accordance with the invention using a visual indicator of the vertical direction.
FIG. 5C is a side view of the image orientation unit of the endoscopic assembly of FIGS. 5A-B.

Though, in some advantageous embodiments, the assembly uses the above described determination of rotation relative to the direction of gravity to automatically level the image, in other embodiments, this is used to provide the surgeon with an indicator of vertical without reorientating the endoscopic image, as shown in FIGS. 5A-C. This allows surgeons, some of whom have become accustomed to reorienting the camera manually during a procedure and do not necessarily require the image to be automatically corrected for them, to continue the practice of adjusting the camera themselves by using the indicator as an aid in determining how much rotation is needed in order to obtain a truly upright image.

For example, referring first to Figure C, the orientation unit 88 includes a ring a light emitting diodes 90. Each diode in the array 90 can be individually illuminated based on a signal produced by the accelerometer 18 arranged in the housing. As shown in FIG. 5A, a particular illuminated diode 92 acts as an indicator of the up direction 94 of the endoscopic image. Depending on the attitude of the endoscope, this up-direction 94 is generally not aligned with the physical up-direction 96 of the camera head 12. Thus, as illustrated in FIG. 5B, the illuminated diode 92 tells the user through what angle 98 to rotate the camera head 12 in order to obtain an upright image. Other indicators of vertical may be employed besides light emitting diodes, such as, for example, a marker mounted to the unit such that it is rotatable by an actuator according to signals received from the accelerometer 18.

Typically, the orientation units described above are coupled tightly to the eyepiece 32 of the endoscope, such that the accelerometer 18 moves in direct correspondence with the endoscope. However, in other embodiments, rotation between the orientation unit and the eyepiece 32 may be provided if the orientation unit includes another rotation sensor for sensing the relative rotation. For example, in some embodiments, a rotating coupling with an encoder to monitor the relative rotation between the endoscope and the orientation unit (including the accelerometer 18) is employed. This accelerometer senses the rotation of the orientation unit and not the endoscope, but the encoder would relate the roll of the orientation unit to the roll of the endoscope. The accelerometer would also still provide information about the endoscope inclination (i.e., pitch), as this would still be the same for both the scope and the orientation unit. It should also be noted that any rotary encoder used to sense rotation could be either incremental or absolute.

As previously noted, the initial arrangement of the endoscope, orientation unit, and camera head must be determined. This serves as the reference configuration, and all changes in configuration occurring during a procedure are measured relative to this reference. Typically, a user would orient the endoscope, orientation unit, and camera according to a reference orientation at the beginning of each use. In some cases, sensors are employed to automatically detect the relative arrangement of the system components based on indicators or markers so that the user does not have to perform any manual alignment.

Figure 6:
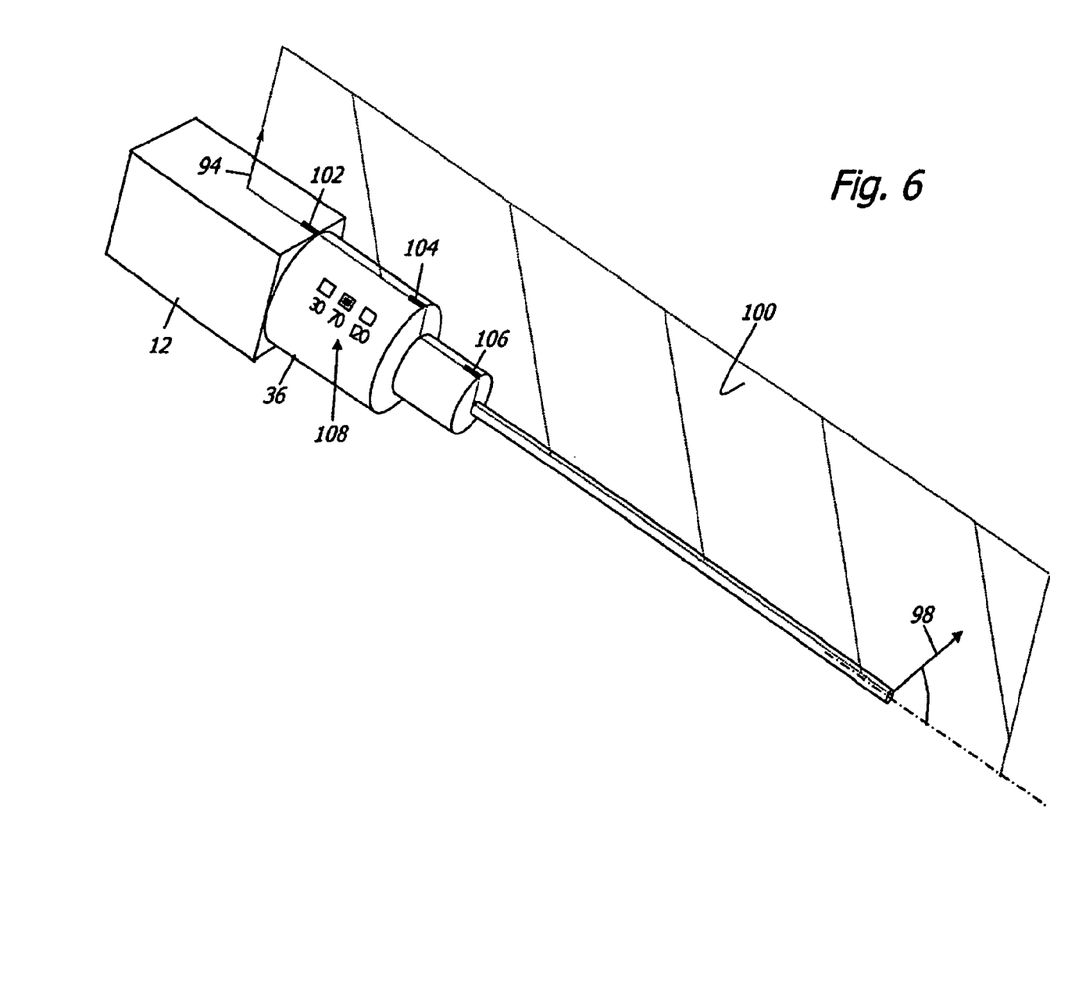
FIG. 6 is an isometric view of the endoscopic system of FIGS. 5A-B with a scope having an off-axis view vector.

For endoscopes with fixed, off-angle viewing direction, such as thirty or seventy degrees, the leveling or indication of vertical performed by the orientation unit would either be specific to the off-angle, or it would have an adjustable setting. As illustrated in FIG. 6, the user lines up the orientation unit according to an initial reference configuration, in which the up directions 94 of the camera head 12, the orientation unit 36, and the off-angle viewing direction 98 of the endoscope lie in the same plane 100. The up directions are indicated by alignment notches 102, 104, 106, and the unit 36 is precalibrated according to a mathematical framework, such as that disclosed in U.S. Patent Application Nos. 2005/0154260 and 2005/0228230 by Schara, et al., the specifications of which is hereby incorporated herein in their entireties by reference. If the unit 36 has an adjustable setting, the user can select the angle for the endoscope with a set of buttons 108. The processor 16 then adjusts the image orientation parameters as taught in the aforementioned applications according to the selected setting.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A coupling assembly for connecting a scope and image sensor housing, comprising:
    a image orientation unit having first and second ends, said unit having a first coupler section located at the first end of said unit for coupling said unit to a scope and a second coupler section located at the second end of said unit for coupling said unit to an image sensor housing;
    an optical assembly at least partly arranged in said unit for transmitting images therethrough, said optical assembly having at least one rotatable optical element that rotates the optical images;
    a rotation sensor for monitoring rotation of said optical element and generating a first signal therefor;
    an accelerometer arranged in said image orientation unit for monitoring the rotation of said unit and generating a second signal therefor; and
    a processor connected to said rotation sensor and said accelerometer for receiving the first and second signals and, at least partly based on the first and second signals, calculating the orientation of the images relative to the direction of gravity.

2. The assembly of claim 1, further comprising an actuator for rotating said optical element, wherein said actuator is connected to said processor to receive a signal from said processor indicating the amount to rotate said optical element in order to level said images.

3. The assembly of claim 2, wherein said actuator comprises a motor, further comprising:
    an optical element housing in which said optical element is at least partly disposed;
    a first gear coupled to said motor and rotated thereby;
    a second gear driven by said first gear and coupled to said optical element housing such that said optical element is rotated by rotation of said second gear.

4. The assembly of claim 1, wherein said optical element comprises a dove prism.

5. The assembly of claim 1, wherein said optical element comprises a K prism.

6. The assembly of claim 1, wherein said optical assembly further includes an image reverser.

7. The assembly of claim 6, wherein said image reverser comprises a prism.

8. The assembly of claim 1, further comprising a rotatable image sensor for receiving the images transmitted by said optical assembly, wherein said image sensor is connected to said processor and rotated thereby based on the first and second signals.

9. The assembly of claim 1, wherein said rotation sensor comprises a rotary encoder.

10. The assembly of claim 1, wherein said unit further includes a visual indicator that indicates the direction of vertical based on the signal provided by the accelerometer.

11. The assembly of claim 10, wherein said visual indicator comprises an array of diodes, wherein said diodes are individually illuminated to indicate the direction vertical.

12. The assembly of claim 1, wherein said accelerometer senses the inclination of said unit relative to the direction of gravity and communicates a signal therefor to said processor.

13. An assembly connecting a scope and an image sensor housing, comprising:
    an image orientation unit having first and second ends;
    a scope coupled to the first end of said image orientation unit;
    an image sensor housing coupled to the second end of said image orientation unit;
    an optical assembly at least partly arranged in said unit for transmitting images therethrough, said optical assembly having at least one rotatable optical element that rotates the optical images;
    a rotation sensor for monitoring rotation of said optical element and generating a first signal therefor;
    an accelerometer arranged in said image orientation unit for monitoring the rotation of said unit and generating a second signal therefor; and a processor connected to said rotation sensor and said accelerometer for receiving the first and second signals and, at least partly based on the first and second signals, calculating the orientation of the images relative to the direction of gravity;

wherein said image orientation unit is detachably coupled between said scope and said image sensor.

14. The assembly of claim 13, wherein the scope is an endoscope.

15. The assembly of claim 14, wherein the image sensor housing is a camera head.

16. The assembly of claim 13, wherein the scope has a longitudinal axis and a view vector angularly offset from the longitudinal axis.

17. The assembly of claim 13, wherein the scope has a view vector with a variable direction of view.

18. The assembly of claim 13, wherein the scope is rigidly connected to said orientation unit.

19. The assembly of claim 13, wherein the camera head is rigidly connected to said orientation unit.

20. The assembly of claim 13, further comprising an actuator for rotating said optical element, wherein said actuator is connected to said processor to receive a signal from said processor indicating the amount to rotate said optical element in order to level said images.

21. The assembly of claim 20, wherein said actuator comprises a motor, further comprising:
an optical element housing in which said optical element is at least partly disposed;
a first gear coupled to said motor and rotated thereby;
a second gear driven by said first gear and coupled to said optical element housing such that said optical element is rotated by rotation of said second gear.

22. The assembly of claim 13, further comprising a rotatable image sensor for receiving the images transmitted by said optical assembly, wherein said image sensor is connected to said processor and rotated thereby based on the first and second signals.

23. The assembly of claim 13, wherein said unit further includes a visual indicator that indicates the direction of vertical based on the signal provided by the accelerometer.

24. The assembly of claim 23, wherein said visual indicator comprises an array of diodes, wherein said diodes are individually illuminated to indicate the direction vertical.

25. The assembly of claim 13, wherein said accelerometer senses the inclination of said unit relative to the direction of gravity and communicates a signal therefor to said processor.

* * * * *